United States Patent [19]

Saulnier et al.

[11] Patent Number: 4,965,348

[45] Date of Patent: Oct. 23, 1990

[54] DIMERIC EPIPODOPHYLLOTOXIN GLUCOSIDE DERIVATIVES

[75] Inventors: Mark G. Saulnier, Middletown; David R. Langley, Meriden, both of Conn.

[73] Assignee: Bristol-Myers Company, New York, N.Y.

[21] Appl. No.: 354,956

[22] Filed: May 19, 1989

[51] Int. Cl.$^5$ .................... C07H 15/24; C07H 15/20; C07H 15/26

[52] U.S. Cl. ................................. 536/17.2; 536/17.3; 536/17.4; 536/18.1; 536/18.2; 536/17.5; 514/27

[58] Field of Search .................... 536/17.2, 17.3, 17.4, 536/17.5, 18.1, 18.2; 514/27

[56] References Cited

U.S. PATENT DOCUMENTS

| | | | |
|---|---|---|---|
| 3,524,844 | 8/1970 | Keller-Juslen | 536/18.1 |
| 4,567,253 | 1/1986 | Durst et al. | 536/18.1 |
| 4,716,221 | 12/1987 | Umezawa et al. | 536/17.2 |
| 4,853,467 | 8/1989 | Vyas et al. | 536/17.9 |
| 4,868,291 | 9/1989 | Saulnier et al. | 536/18.1 |
| 4,874,851 | 10/1989 | Vyas et al. | 536/17.2 |
| 4,888,419 | 12/1989 | Saulnier et al. | 536/18.1 |
| 4,912,204 | 3/1990 | Ohnuma et al. | 536/18.1 |
| 4,916,217 | 4/1990 | Saulnier | 536/17.1 |

FOREIGN PATENT DOCUMENTS

| | | |
|---|---|---|
| 0320988 | 6/1989 | European Pat. Off. . |
| 63-150293 | 6/1988 | Japan . |
| 6617379 | 6/1967 | Netherlands . |
| 2207674 | 2/1989 | United Kingdom . |
| 8600018 | 1/1986 | World Int. Prop. O. . |

OTHER PUBLICATIONS

Levy, R. K. et al., "Antitumor Agents LXII: Synthesis and Biological Evaluation of Podophyllotoxin Esters and Related Derivatives", *J. Pharm. Sci., 1983, 72(10):1158-1161.*

Wakelin, L. P. G.; "Polyfunctional DNA Intercalating Agents", *Medicinal Res. Rev.,* 1986, 6(3):275–340.

Primary Examiner—Ronald W. Griffin
Assistant Examiner—Nancy S. Carson
Attorney, Agent, or Firm—Mollie M. Yang

[57] ABSTRACT

The present invention provides novel dimers of epipodophyllotoxin glucosides wherein the two units are connected via a diacyl linker. These compounds have useful property as tumor inhibiting agents.

10 Claims, No Drawings

DIMERIC EPIPODOPHYLLOTOXIN GLUCOSIDE DERIVATIVES

BACKGROUND OF THE INVENTION

1. Field of the Invention

The present invention relates to dimeric epipodophyllotoxin glucoside derivatives, to their therapeutic anti-tumor use, and to pharmaceutical dosage forms containing these new agents.

2. Description of the Related Art

Etoposide (VP-16, Ia) and teniposide (VM-26, Ib) are clinically useful anticancer agents derived from the naturally occurring lignan, podophyllotoxin (II). The numbering system used for nomenclature purposes is shown in Formula II. Etoposide and teniposide are 4′-demethyl epipodophyllotoxin derivatives; epipodophyllotoxin being the epimer of podophyllotoxin at the 4-position. Etoposide and teniposide are active in the treatment of a variety of cancers including small cell lung cancer, non-lymphocytic leukemia, and non-seminomatous testicular cancer (AMA Drug Evaluation, 5th Edition, American Medical Association, 1983, Chicago, Ill., p. 1554-5).

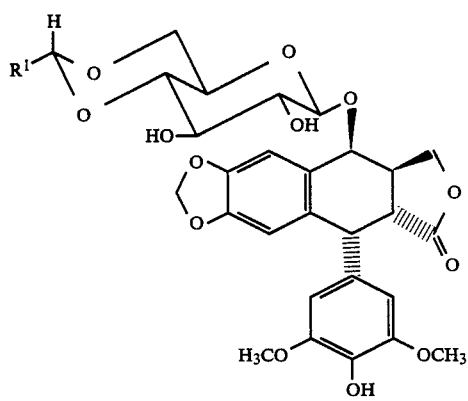

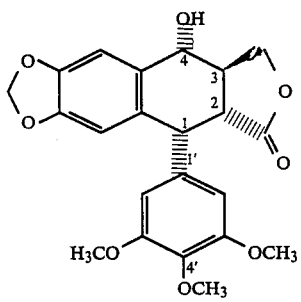

Ia $R^1$ = $CH_3$
Ib $R^1$ = 2-theinyl

It has been postulated that one of the mechanisms by which etoposide exerts its cytotoxic activity involves stablilizing a DNA-topoisomerase II complex leading eventually to DNA strand breaks. This type of action has also been observed for other antitumor agents, e.g. adriamycin, mitoxantrone, and m-AMSA which, unlike etoposide, are DNA intercalators. Dimeric forms of adriamycin, mitoxantrone, and the intercalating 9-aminoacridine portion of m-AMSA have been prepared as potential bis-intercalators for DNA. Podophyllotoxin derivative of formula III was reported in J. Pharm. Sci., 1983, 72:1158-61; however, this compound was inactive against P388 leukemia.

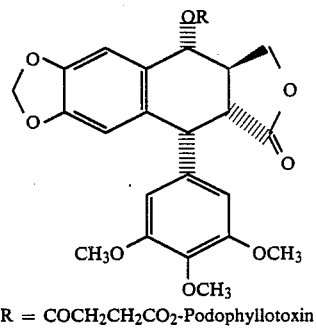

R = $COCH_2CH_2CO_2$-Podophyllotoxin

SUMMARY OF THE INVENTION

The present invention provides compounds of formula IV

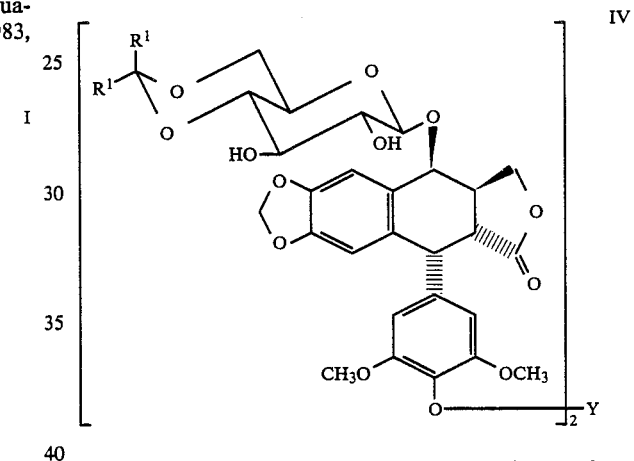

wherein $R^1$ and $R^2$ are each $C_{1-10}$alkyl; $R^1$ and $R^2$ together with the carbon to which they are attached represent $C_{5-6}$ cycloalkyl; or $R^1$ is H and $R^2$ is selected from the group consisting of $C_{1-10}$alkyl, $C_{2-10}$alkenyl, $C_{3-6}$-cycloalkyl, furyl, thienyl, $C_{6-10}$aryl, and $C_{7-14}$aralkyl; and Y is —C(O)— or or —C(O)—a—X—a—C(O)—, wherein a—X—a is selected from the group consisting of $(C_{1-10})$alkylene and $(C_{2-3})$alkylenediamine; or X is selected from the group consisting of $C_{3-6}$ cycloalkyl, $C_{6-12}$ aryl, 5- to 6-membered heteroaryl, and 5- to 6-membered nitrogen containing aliphatic ring; and a is selected from the group consisting of $(C_{1-5})$alkylene and amino$(C_{1-5})$alkylene.

A further aspect of the present invention provides a method for inhibiting mammalian tumor which comprises administering to a tumor-bearing host an antitumor effective dose of a compound of formula IV.

Yet another aspect of the present invention provides a pharmaceutical composition which comprises a compound of formula IV and a pharmaceutically acceptable carrier.

DETAILED DESCRIPTION OF THE INVENTION

As used herein the term "aryl" includes e.g. phenyl, naphthyl and biphenyl; "heteroaryl" includes e.g. pyridyl, furyl, thienyl, pyrrolyl, pyrimidinyl and the like;

"nitrogen containing aliphatic ring" may be for example piperazine, piperidine, pyrrolidine, etc.

In a preferred embodiment of compounds of formula IV, $R^1$ is H and $R^2$ is methyl or 2-thienyl.

In a further preferred embodiment the linker Y is selected from the group consisting of —C(O)—, $C(O)(CH_2)_{1-10}C(O)$—, —$C(O)NH(CH_2)_{2-3}NHC(O)$—, and

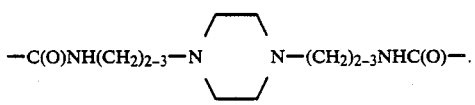

A most preferred linker Y is the group —C(O)NH(CH$_2$)$_2$NHC(O)—.

Compounds of the present invention are dimers of eipipodophyllotoxin glucosides in which the 4'-hydroxyl groups of the two epipodophyllotoxin glucoside units are connected via a diacyl linker to form diesters or biscarbamates, or via the carbonyl radical to form biscarbonates.

The epipodophyllotoxin glucosides starting material and their preparation are disclosed in U.S. Pat. No. 3,524,844. Diacids and their acylating equivalents, and bis amines are either commercially available or may be readily prepared by conventional methods known in the art.

Dimeric epipodophyllotoxin glucosides having a diester linkage are prepared by reacting a compound of formula V

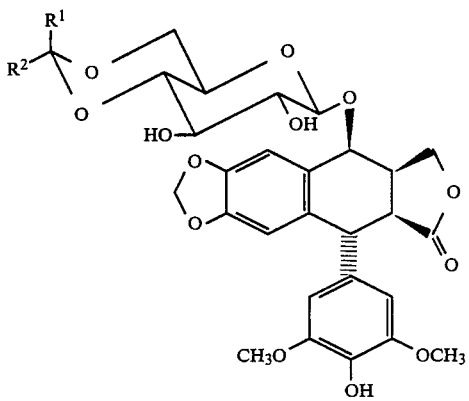

wherein $R^1$ and $R^2$ are as defined above, with approximately 0.5 equivalent of a dicarboxylic acid $HO_2C$—a—X—a—$CO_2H$ wherein a—X—a is ($C_{1-10}$)alkylene; or X is as previously defined, and a is direct bond or ($C_{1-5}$)alkylene; or an acylating equivalent thereof. Acylating agent may be the carboxylic acid, preferably used in conjunction with a condensing agent such as dicylohexylcarbodiimide (DCC), symmetrical or mixed acid anhydride, active ester, active amide, acid halide, and the like. The reaction is preferably carried out in an anhydrous aprotic organic solvent such a acetonitrile, methylene chloride, acetone, and tetrahydrofuran. An acid acceptor is preferably included in the reaction mixture; suitable acid acceptor may be for example tertiary amine bases such as diisopropylethylamine, triethylamine, pyridine and the like, or inorganic bases such as potassium carbonate and sodium carbonate. The reaction may be conducted at temperatures from about 0° to about 50° C.; the reaction temperature and time will depend on the nature of the reactants employed. In our experience we have found that reaction between an acid chloride and the epipodophyllotoxin glucoside may be conveniently carried out at room temperature and the reaction is generally complete within 24 hours. If the acid chloride is replaced by phosgene or trichloromethyl chloroformate, the carbonate dimer (IV, Y=—C(O)—) is obtained.

Bis-carbamate linked dimers are prepared by reacting compound of formula V with phosgene in the presence of a base such as those recited above to generate the corresponding 4'-chloroformate which is trapped in situ by the addition of a bis amine reagent. Bis amines are compounds having two nucleophilic nitrogen atoms capable of displacing the chloride of the chloroformate intermediate and may include, but are not limited to ethylenediamine, propylenediamine, piperazine, 1,4-bis-(aminopropylene)piperazine, etc. The bis amine is used in half equivalent relative to the epipodophyllotoxin glucoside reactant. The reaction may be carried out under conditions described above for the preparation of the diester.

It will be appreciated that the above general procedure may be modified according to the particular reactants used. The reaction solvent, reagents, and conditions may be ascertained by one skilled in the art without undue experimentation.

Biological Activity

Representative compounds of the present inventions were evaluated against transplantable murine P388 leukemia.

Female CDF$_1$ mice were implanted intraperitoneally with a tumor inoculum of $10^6$ ascites cells of P388 leukemia and treated with various doses of a test compound. A group of four mice was used for each dose level. Ten mice treated with saline were included in each series of experiments as negative control and six etoposide treated mice were included as positive control. The drugs were administered intraperitoneally on days 5 and 8 (day 0 being the day of tumor implantation). The length of the experiments ranges from 47 days to 51 days. At the end of each experiment the number of survivors for each group was noted. The mean survival time for each group of mice was determined and antitumor activity was expressed as % T/C which is the ratio of the medium survival time (MST) of drug-treated group to the MST of saline-treated control group. A compound showing a % T/C value of 125 of greater is generally considered to have significant antitumor activity in the P388 test. Table I presents the results of the above-described evaluation; included in the Table are the maximum % T/C and the dose showing the maximum effect.

TABLE I

| Antitumor Activity Against P388 Leukemia | | |
|---|---|---|
| Compound | Dose (mg/kg/dose) | % T/C |
| Ex. 1 | 200 | 175 |
| Ex. 2 | 200 | 130 |
| Etoposide | 80 | 260 |
| Ex. 3 | 200 | 160 |
| Etoposide | 100 | 270 |
| Ex. 4 | 280 | 365 |
| Etoposide | 100 | 295 |
| Ex. 5 | 150 | 317 |
| Etoposide | 150 | >567 |
| Ex. 6 | 150 | 130 |

TABLE I-continued

| Antitumor Activity Against P388 Leukemia | | |
|---|---|---|
| Compound | Dose (mg/kg/dose) | % T/C |
| Etoposide | 150 | >480 |

Compound of Example 4 was also evaluated against subcutaneously implanted B16 melanoma in female C57B/6 mice. Ten mice were used for each dose level of the test compound, etoposide and saline control; and the drug was administered intraperitoneally on days 1, 5 and 9. Compound of Example 4 showed a maximum % T/C of 149 at 240 mg/kg/dose and etoposide in the same experiment showed a maximum % T/C of 230 at 120 mg/kg/dose.

As indicated by the mouse tumor data provided above, compounds of present invention are useful as antitumor agents for inhibition of mammalian malignant tumors such as P-388 leukemia and B16 melanoma.

The invention includes within its scope pharmaceutical compositions containing an effective tumor-inhibiting amount of a compound of the present invention in combination with an inert pharmaceutically acceptable carrier or diluent. Such compositions may also contain other active antitumor agents and may be made up in any pharmaceutical form appropriate for the desired route of administration. Examples of such compositions include solid compositions for oral administration such as tablets, capsules, pills, powders and granules, liquid compositions for oral administration such as solutions, suspensions, syrups or elixirs and preparations for parenteral administration such as sterile solutions, suspensions or emulsions. They may also be manufactured in the form of sterile solid compositions which can be dissolved in sterile water, physiological saline or some other sterile injectable medium immediately before use.

For use as an antitumor agent, optimal dosages and regimens for a given mammalian host can be readily ascertained by those skilled in the art. It will, of course, be appreciated that the actual dose used will vary according to the particular compound selected, composition formulated, the route of administration and the particular situs, host and disease being treated Many factors that modify the action of the drug will be taken into account including age, weight, sex, diet, time of administration, route of administration, rate of excretion, condition of the patient, drug combinations, reaction sensitivities and severity of the disease.

In the following examples, proton nuclear magnetic resonance (NMR) spectra (using $CDCl_3$ or $D_2O$ as an internal reference) were recorded on a Bruker WM360 spectrometer. Infrared spectra (IR) were determined on a Perkin-Elmer 1800 Fourier Transform Infrared Spectrophotometer. "Flash chromatography" refers to the method described by Still (Still, W. C.; Kahan, M.; Mitra, A.; *J. Org. Chem.*, 1978, 43, 2923) and was carried out using E. Merck silica gel (230–400 mesh). The following examples serve only to illustrate the invention without limiting the scope of the invention which is defined by the claims.

Example 1: Bis Etoposide (4'-Adipate)

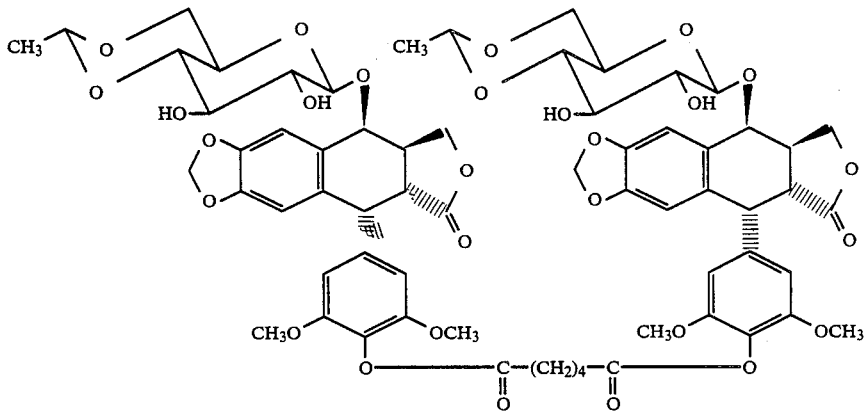

A magnetically stirred solution of dry etoposide (2.25 g, 3.82 mmol) in dry acetonitrile (210 ml) under $N_2$ was treated with N,N-diisopropylethylamine (0.82 ml, 4.71 mmol) followed by the slow addition of neat adipoyl chloride (362 mg, 1.98 mmol) over 2 min. The reaction mixture was stirred at room temperature for 18 hours, concentrated in vacuo to a volume of 50 ml, diluted with ethyl acetate (125 ml), and partitioned with pH 5 phosphate buffer (125 ml). The organic layer was washed with $H_2O$ (50 ml) and brine (100 ml), dried ($Na_2SO_4/MgSO_4$), and filtered through Celite. The filtrate was treated with 10 ml hexane and cooled to $-10°$ C. to produce 782 mg (32%) of the pure title compound as a colorless solid. A second crop gave 550 mg (22%) of additional product.

IR (KBr) 1770, 1736, 1602, 1507, 1486, 1465, 1421, 1381, 1338, 1237, 1160, 1040, 1004 $cm^{-1}$.

360 MHz $^1H$ NMR ($CDCl_3$) δ 6.81 (s, 2H), 6.54 (s,2H), 6.25 (br s, 4H), 5.97 (dd, 4H), 4.88 (d, 2H, J=3.5 Hz), 4.73 (q, 2H, J=4.9 Hz), 4.64 (d, 2H, J=7.5 Hz), 4.62 (d, 2H, J=5.2 Hz), 4.41 (m, 2H), 4.22 (m, 2H), 4.15 (dd, 2H), 3.74 (m, 2H), 3.64 (S, 12H), 3.56 (m, 2H), 3.43 (m, 2H), 3.36-3.31 (m, 4H), 3.25 (dd, 2H, J=5.1 and 14.1 Hz), 2.90-2.82 (m, 2H), 2.64 (d, 2H, OH, J=2.2 Hz), 2.61 (m, 4H), 2.35 (d, 2H, OH, J=2.7 Hz), 1.86 (m, 4H), 1.38 (d, 6H, J=4.9 Hz).

mass spectrum (FAB), m/e, 1287 (M+ +H)

Anal. calcd for $C_{64}H_{70}O_{28}$: C, 59.72; H, 5.48.

Found*: C, 59.42; H, 5.68.

*corrected for 0.78% $H_2O$ as determined by K.F. Analysis.

Example 2: Bis Etoposide (Sebacoate)

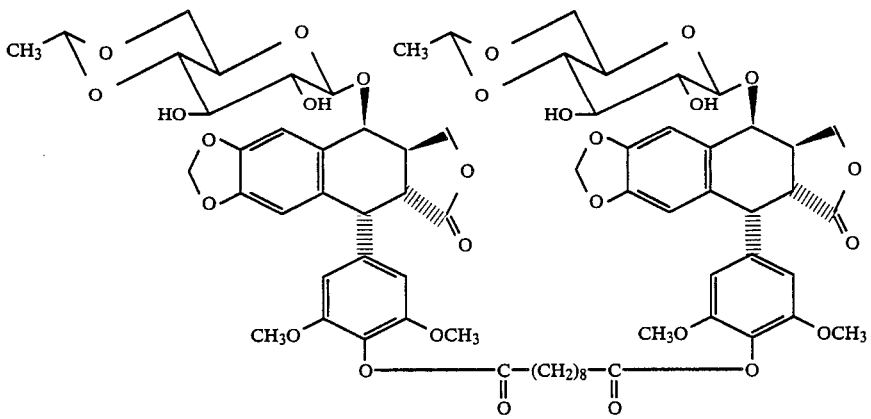

-continued

Using the procedure described in example 1 with etoposide (2.40 g, 4.08 mmol), N,N-diisopropylethylamine (0.88 ml, 5.05 mmol), and sebacoyl chloride (505 mg, 2.11 mmol) there was obtained 2.10 g (76.5%) of the pure title compound as a colorless solid.

IR (KBr) 1770, 1737, 1602, 1506, 1486, 1465, 1421, 1380, 1337, 1236, 1159, 1132, 1039, 1004 cm$^{-1}$.

360 MHz $^1$H NMR (CDCl$_3$) δ 6.81 (s, 2H), 6.53 (s, 2H), 6.24 (br s, 4H), 5.96 (d, 4H), 4.88 (d, 2H, J=3.3 Hz), 4.73 (q, 2H, J=4.8 Hz), 4.63–4.60 (m, 4H), 4.40 (m, 2H), 4.21 (m, 2H), 4.16 (dd, 2H), 3.70 (m, 2H), 3.63 (s, 12H), 3.55 (m, 2H), 3.40 (m, 2H), 3.35–3.24 (m, 6H), 2.87–2.80 (m, 2H), 2.80 (br s, 2H, OH), 2.63 (br s, 2H, OH), 2.53 (t, 4H), 1.72–1.66 (m, 4H), 1.37 (d, 6H, J=4.8 Hz), 1.37–1.33 (m, 8H).

mass spectrum (FAB), m/e, 1343 (M$^+$+H).

Using the procedure described in example 1 with etoposide (2.10 g, 3.57 mmol), N,N-diisopropylethylamine, and diphosgene (362 mg, 1.83 mmol) there was obtained 0.62 g (29%) of the pure title compound following workup and flash chromatography on silica gel with 7–8% CH$_3$OH in CH$_2$Cl$_2$.

IR (KBr) 1775, 1604, 1507, 1486, 1466, 1422, 1341, 1237, 1197, 1159, 1131, 1098, 1077, 1037, 1002, 931 cm$^{-1}$.

360 MHz $^1$H NMR (CDCl$_3$) δ 6.81 (s, 2H), 6.52 (s, 2H), 6.26 (br s, 4H), 5.97 (d, 4H), 4.88 (d, 2H, J=3.3 Hz), 4.73 (q, 2H, J=5.0 Hz), 4.65–4.61 (m, 4H), 4.39 (m, 2H), 4.22–4.14 (m, 4H), 3.71 (m, 2H), 3.70 (s, 12H), 3.55 (m, 2H), 3.42 (m, 2H), 3.33–3.30 (m, 4H), 3.25 (dd, 2H, J=5.2 and 14.2 Hz), 2.90–2.82 (m, 2H), 2.69 (brs, 2H, OH), 2.39 (brs, 2H, OH), 1.37 (d, 6H, J=5.0 Hz).

Example 3: Bis Etoposide 4'-Carbonate

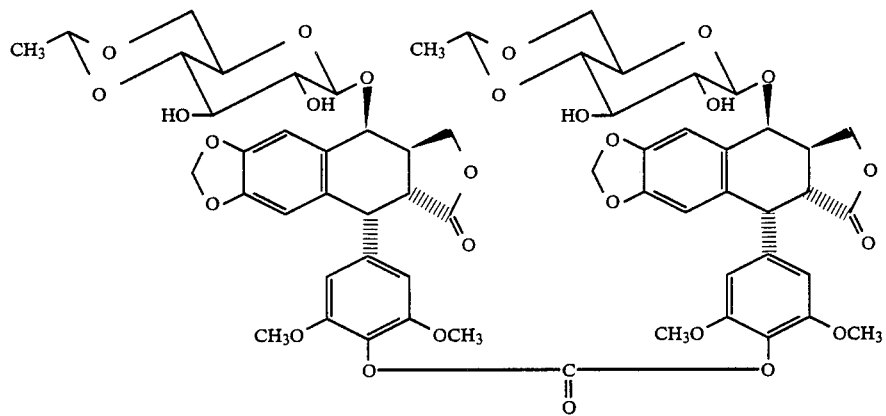

mass spectrum (FAB), m/e, 1202.3467.
C$_{59}$H$_{62}$O$_{27}$ requires 1202.3479.

Example 4: Bis Etoposide (4'-Ethylene Diamine Carbamate)

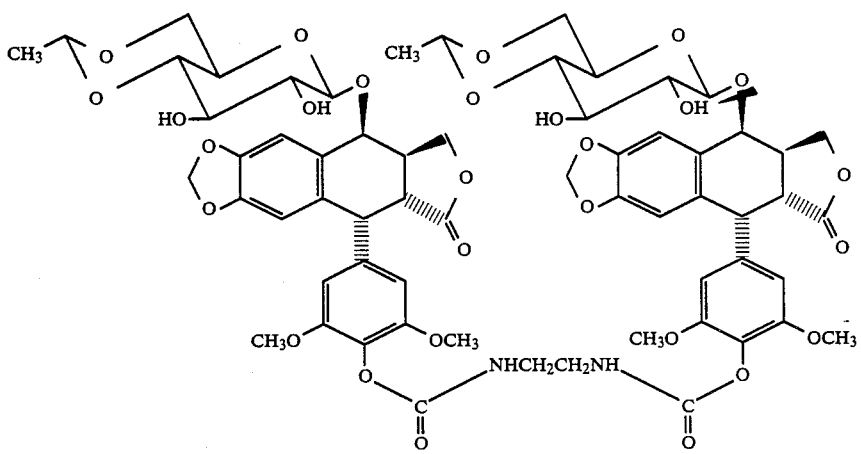

A magnetically stirred solution of dry etoposide (2.00 g, 3.40 mmol) in dry acetonitrile (225 ml) under N₂ at 0° C. was treated with N,N-diisopropylethylamine (1.30 ml, 7.48 mmol) and then a solution of phosgene (1.93M in toluene; 1.94 ml, 3.74 mmol) was added rapidly via syringe. After 5 minutes at 0° C., the reaction mixture was treated with ethylenediamine (113 μm, 1.70 mmol). After 1.5 hours the solvent was removed in vacuo and the solid residue was dissolved in ethyl acetate (300 ml) and partitioned with 1% aqueous HCl (200 ml). The organic layer was washed with H₂O (150 ml), saturated aqueous sodium bicarbonate (150 ml), H₂O (150 ml), and brine (150 ml), and dried (MgSO₄). Flash chromatography on silica gel using 5% CH₃OH in CH₂Cl₂ elution provided 1.12 g (51%) of the pure titled compound as a colorless solid.

IR (KBr) 1775, 1737, 1604, 1508, 1490, 1470, 1430, 1340, 1240, 1145, 1133, 1100, 1080, 1043, 1010 cm⁻¹.

300 MHz ¹H NMR (CDCl₃/drop d6-DMSO) δ 6.88 (s, 2H), 6.60, (s, 2H), 6.33 (brs, 4H), 6.05 (d, 4H), 4.96 (d, 2H, J=3.3 Hz), 4.82 (q, 2H, J=4.9 Hz), 4.71 (d, 2H, J=7.7 Hz), 4.68 (d, 2H, J=5.3 Hz), 4.48 (m, 2H), 4.31–4.22 (m, 4H), 3.79 (m, 2H), 3.75 (S, 12H), 3.64 (m, 2H), 3.53–3.47 (m, 6H), 3.42–3.30 (m, 6H), 2.99–2.90 (m, 2H), 2.84 (br s, 2H, OH), 2.59 (br s, 2H, OH), 1.46 (d, 6H, J=4.9 Hz).

mass spectrum (FAB), m/e, 1289.4009 (M⁺+H). C₆₂H₆₈N₂O₂₈ requires 1289.4037.

Example 5: Bis Etoposide (4'-(Bis-Aminopropylpiperazine)

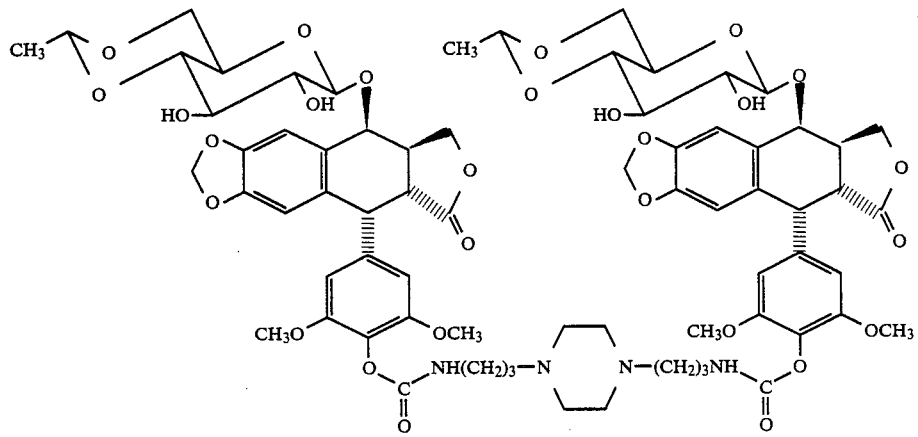

The procedure described in example 4 was followed using etoposide (2.00 g, 3.40 mmol), dry acetonitrile (225 ml), N,N-diisorpopylethylamine (1.42 ml, 8.16 mmol), phosgene (1.93M in toluene; 2.11 ml, 4.08 mmol), and 1,4-bis(3-aminopropyl)piperazine (0.35 ml, 1.70 mmol). After 30 minutes the solvent was removed in vacuo. and the residue was dissolved in CH₂Cl₂ (200 ml) and partitioned with saturated aqueous sodium bicarbonate (200 ml), H₂O (200 ml), and brine (200 ml) and dried (MgSO₄). Flash chromatography on silica gel using 10% CH₃OH in CH₂Cl₂ elution provided 2.43 g (73%) of the pure title compound as a colorless solid.

IR (KBr) 1775, 1740, 1605, 1510, 1493, 1470, 1430, 1390, 1340, 1240, 1218, 1166, 1135, 1100, 1080, 1040, 1010, 937 cm⁻¹.

Partial 300 MHz ¹H NMR (CDCl₃) δ 6.80 (s, 2H), 6.52 (s, 2H), 6.23 (br s, 4H), 5.96 (d, 4H), 4.88 (d, 2H), 4.72 (q, 2H), 4.65–4.61 (m, 4H), 4.39 (m, 2H), 4.22–4.14 (m, 4H), 3.64 (s, 12H), 1.37 (d, 6H, J=5 Hz).

mass spectrum (FAB), m/e, 1429 (M⁺+H). C₇₀H₈₄N₄O₂₈ requires M⁺=1428.

Example 6: Bis Etoposide (4'-(1,3-Diaminopropyl) Carbamate)

-continued

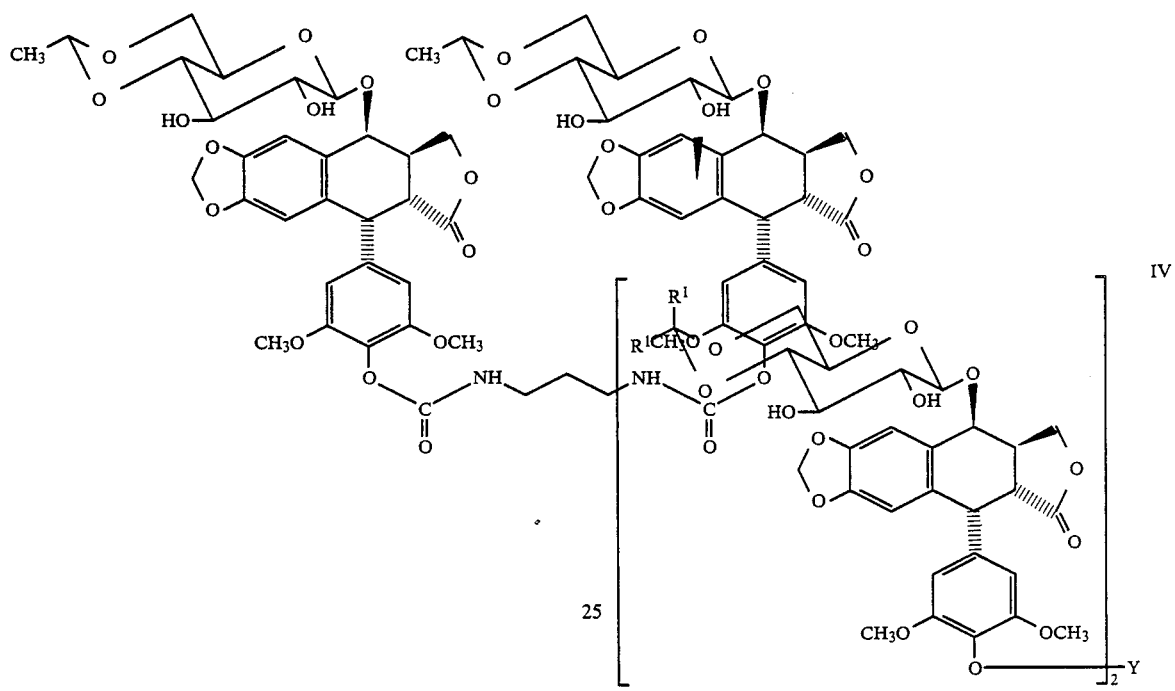

The procedure described in example 4 was followed using etoposide (2.00 g, 3.40 mmol), dry acetonitrile (225 ml), N,N-diisopropylethylamine (1.66 ml, 9.51 mmol), phosgene (1.93M in toluene; 2.29 ml, 4.42 mmol), and 1,3-diaminopropane (0.14 ml, 1.68 mmol). After workup and chromatography according to the procedure described in example 4, 1.41 (g (63.5%) of the pure title compound was obtained as a colorless solid.

IR (KBr) 1775, 1737, 1605, 1512, 1490, 1470, 1427, 1340, 1240, 1218, 1165, 1135, 1100, 1080, 1040, 1007, 933 cm$^{-1}$.

Partial 300 MHz $^1$H NMR (CDCl$_3$) δ 6.79 (s, 2H), 6.52 (s, 2H), 6.23 (br s, 4H), 5.95 (d, 4H), 4.87 (d, 2H, J=3.3 Hz), 4.73 (q, 2H, J=5 Hz), 4.65-4.59 (m, 4H), 4.39 (m, 2H), 4.22-4.12 (m, 4H), 3.76 (m, 2H), 3.64 (s, 12H), 3.58-3.20 (m, 14H), 2.90-2.82 (m, 2H), 1.36 (d, 6H, J=5 Hz).

mass spectrum (FAB), m/e, 1303.4216. C$_{63}$H$_{70}$N$_2$O$_{28}$ requires 1303.4193.

EXAMPLE 7

If the general procedure described in Examples 1-6 are repeated using teniposide instead of etoposide, the corresponding teniposide dimers will be obtained.

What is claimed is:
1. A compound having the formula wherein R$^1$ and R$^2$ are each C$_{1-10}$alkyl; or R$^1$ and R$^2$ together with the carbon to which they are attached represent C$_{5-6}$ cycloalkyl; or R$^1$ is H and R$^2$ is selected from the group consisting of C$_{1-10}$alkyl, C$_{2-10}$alkenyl, C$_{3-6}$cycloalkyl, furyl, thienyl, C$_{6-10}$aryl, and C$_{7-14}$aralkyl; and Y is —C(O)— or —C(O)—a—X—a—C(O)—, wherein a—X—a is selected from the group consisting of (C$_{1-10}$)alkylene and (C$_{2-3}$)alkylenediamine; or X is selected from the group consisting of C$_{3-6}$cycloalkyl, C$_{6-12}$aryl, 5- to 6-membered heteroaryl, and 5- to 6-membered nitrogen containing aliphatic ring; and a is selected from the group consisting of (C$_{1-5}$)alkylene and amino(C$_{1-5}$)alkylene.

2. A compound of claim 1 wherein R$^1$ is H and R$^2$ is methyl or 2-thienyl.

3. A compound of claim 1 wherein Y is selected from the group consisting of —C(O)—, —C(O)—a—X—a—C(O)— wherein a—X—a is selected from the group consisting of (C$_{1-10}$)alkylene and (C$_{2-3}$)alkylenediamine; or X is piperazine and a is amino(C$_{1-5}$)alkylene.

4. A compound of claim 1 wherein R$^1$ is H and R$^2$ is methyl.

5. A compound of claim 4 wherein Y is —C(O)—.

6. A compound of claim 4 wherein Y is —C(O)—(CH$_2$)$_4$—C(O)—.

7. A compound of claim 4 wherein Y is —C(O)—(CH$_2$)$_8$—C(O)—.

8. A compound of claim 4 wherein Y is —C(O)NH(CH$_2$)$_2$NHC(O)—.

9. A compound of claim 4 wherein Y is —C(O)NH(CH$_2$)$_3$NHC(O)—.

10. A compound of claim 4 wherein Y is

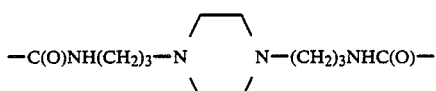

* * * * *

UNITED STATES PATENT AND TRADEMARK OFFICE
CERTIFICATE OF CORRECTION

PATENT NO. : 4,965,348

DATED : October 23, 1990

INVENTOR(S) : Mark G. Saulnier, et al

It is certified that error appears in the above-identified patent and that said Letters Patent is hereby corrected as shown below:

Column 2, formula IV spanning lines 25-40: the portion of the formula reading

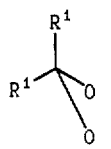   should read   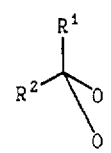

Columns 11 and 12, the formula for compound of Example 6 should read

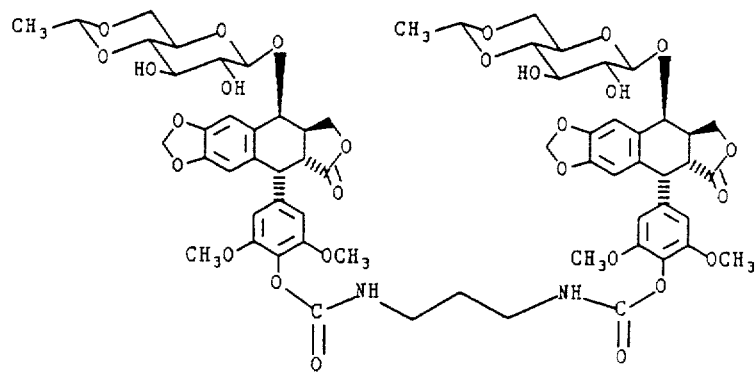

UNITED STATES PATENT AND TRADEMARK OFFICE
CERTIFICATE OF CORRECTION

PATENT NO. : 4,965,348

DATED : October 23, 1990

INVENTOR(S) : Mark G. Saulnier, et al

It is certified that error appears in the above-identified patent and that said Letters Patent is hereby corrected as shown below:

Column 12, in claim 1 formula IV should read

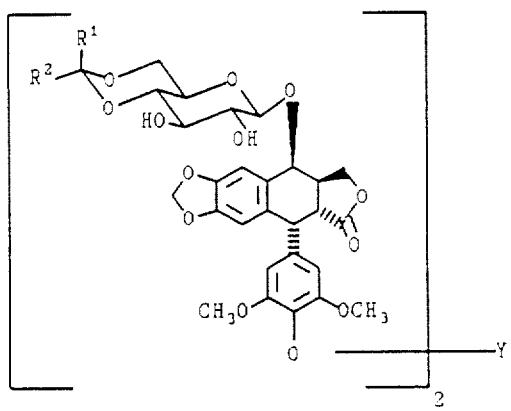

Signed and Sealed this

Eleventh Day of August, 1992

*Attest:*

DOUGLAS B. COMER

*Attesting Officer*  *Acting Commissioner of Patents and Trademarks*